United States Patent [19]
Urtti et al.

[11] Patent Number: 5,656,292
[45] Date of Patent: Aug. 12, 1997

[54] COMPOSITION FOR PH DEPENDENT CONTROLLED RELEASE OF ACTIVE INGREDIENTS AND METHODS FOR PRODUCING IT

[75] Inventors: Arto Olavi Urtti, Kuopio; Soili Hellevi Peltonen, Rajamäki; Timo Petteri Paronen; Leena Johanna Nakari, both of Kuopio; Jani-Emanuel Vuorenpää, Helsinski, all of Finland

[73] Assignee: Alko Group Ltd., Helsinki, Finland

[21] Appl. No.: 498,341

[22] Filed: Jul. 5, 1995

Related U.S. Application Data

[63] Continuation-in-part of Ser. No. 374,430, Jan. 19, 1995.

[30] Foreign Application Priority Data

Jun. 7, 1994 [FI] Finland ................ 942686

[51] Int. Cl.$^6$ ................ A61K 9/20; A61K 9/26; A61K 9/24; C08B 31/02
[52] U.S. Cl. ................ 424/464; 424/465; 424/470; 424/472; 514/778; 536/102; 536/107; 536/110
[58] Field of Search ................ 424/464, 465, 424/470, 472; 514/778; 536/102, 107, 110

[56] References Cited

U.S. PATENT DOCUMENTS 4,011,392  3/1977  Rudolph et al.

FOREIGN PATENT DOCUMENTS

| | | |
|---|---|---|
| 652281 | 8/1994 | Australia. |
| 656014 | 1/1995 | Australia. |
| 0428965 | 11/1990 | European Pat. Off.. |
| 0638609 | 7/1994 | European Pat. Off.. |
| 9300939 | 1/1993 | WIPO. |
| 9533450 | 6/1995 | WIPO. |

OTHER PUBLICATIONS

Pradeepkumar P. et al, "Evaluation of Preflo Modified Starches as New Direct Compression Excipients.", Pharmaceutical Research, vol. 10, No. 11, (1993).

*Primary Examiner*—Carlos A. Azpuru
*Attorney, Agent, or Firm*—Browdy and Neimark

[57] ABSTRACT

The present invention is related to a composition for pH dependent or pH regulated controlled release of active ingredients especially drugs. The composition consists of a compactible mixture of the active ingredient and starch molecules substituted with acetate and dicarboxylate residues. The preferred dicarboxylate acid is succinate. The average substitution degree of the acetate residue is at least 1 and 0.2–1.2 for the dicarboxylate residue. The starch molecules can have the acetate and dicarboxylate residues attached to the same starch molecule backbone or attached to separate starch molecule backbones. The present invention also discloses methods for preparing said starch acetate dicarboxylates by transesterification or mixing of starch acetates and starch dicarboxylates respectively.

30 Claims, 11 Drawing Sheets

COMPOSITION FOR PH DEPENDENT CONTROLLED RELEASE OF ACTIVE INGREDIENTS AND METHODS FOR PRODUCING IT

CROSS-REFERENCE TO RELATED APPLICATIONS

This is a continuation-in-part of U.S. patent application Ser. No. 08/374,430 filed Jan. 19, 1995, claiming priority from the Finnish patent application Ser. No. 942686 filed on Jun. 7, 1994. The contents of said applications are hereby expressly incorporated by reference.

THE BACKGROUND OF THE INVENTION

1. The Technical Field of the Invention

The present invention is related to compositions for pH dependent controlled release of active ingredients, especially pharmaceutical compositions. The composition is a compact consisting essentially of an active ingredient and a starch acetate dicarboxylate such as succinate. Methods for preparing the composition are also disclosed.

2. The Background of the Invention

Active compounds such as pharmaceuticals, natural health products, fertilizers, herbicides, insecticides, diagnostic reagents are usually not distributed as such, but in the form of more convenient compositions which make the distribution more feasible and allows the preparation of convenient dosage forms for different environmental conditions. Among these environmental conditions the acidity of the environment is an important factor. Pharmaceutical preparations are perhaps the most thoroughly studied compositions. Thus, the background for designing the present pH dependent controlled release compositions is discussed in more detail fundamentally based on the knowledge accumulated in studies with pharmaceutical preparations.

Pharmaceutical preparations typically comprise one or several excipients in addition to the active drug substance or substances. Excipients make the manufacturing of the pharmaceutical dosage forms more feasible and give them suitable physicochemical, biological and biopharmaceutical properties.

The administration of drugs to the human or animal body by way of controlled, sustained or delayed release from a dosage form located in gastrointestinal tract has long been an objective of the pharmaceutical industry. The controlled release dosage forms are used to optimize drug therapy, decrease frequency of dosing, and minimize undesirable side effects. It is generally known that the residence time of a drug in the stomach is largely unpredictable and it depends on the physiology of the individual and the amount and type of food which is taken with a meal. Thus, variations between different patients are particularly significant. On the other hand, the pH conditions in stomach and small intestine are markedly different. Numerous drugs are slightly soluble in acidic environment of stomach and they can be absorbed only when the surrounding pH is greater than 5, as it is in small intestine. Sustained or delayed release properties in dosage forms are primarily intended to extend the release of drug over an prolonged period of time to maintain therapeutic effective blood levels or to decrease the risks of side-effects. In addition, they are used to control the release of a drug at a predetermined point or predetermined points in the gastrointestinal tract. One among these effects is the enteric effect.

By definition, enteric dosage forms are those which remain practically intact in the stomach, but will disintegrate or dissolve and release the drug contents once the product reaches the small intestine. Their prime intention is to delay the release of drugs which are inactivated by the stomach contents, or may cause nausea or bleeding by irritation of the gastric mucosa, or are more preferentially absorbed into blood circulation from small intestine, or have local therapeutic effect in small intestine.

The most widely used technology for obtaining enteric effect is the coating of a compressed tablet by a polymeric film with enteric properties. The powder mixture consisting of drug substance(s) and several excipients is, firstly, mixed, most often also granulated and then compressed into tablets. These tablets are then coated in film coating processes. The preparation of coated products is a multistage process, including several separate mixing, granulation, tabletting and coating phases with numerous and complicated process variables.

Systems based on pH-sensitive polymers tend to be more reliable than those which are dependent of slow dissolution and erosion of the polymer. The most extensively used enteric polymer is cellulose acetate phthalate. Cellulose acetate phthalate films have good enteric properties, but they dissolve only over pH 6 and may thus delay drug release longer than desired. Said cellulose acetate phthalate films are also susceptible to hydrolytic breakdown on storage. Other enteric polymers include e.g. polyvinylacetate phthalate, hydroxy-propylmethylcellulose phthalate, methacrylic acid-methacrylic acid ester copolymer, starch and amylose acetate phthalate, styrene maleic acid copolymer, and cellulose acetate succinate.

The enteric coatings are typically prepared by using either fludized bed or pan coating techniques. The application of enteric polymers is often accomplished by spraying organic solvent based solutions containing from 5 to 30% polymer. Although, water is the solvent of choice in pharmaceutical processes, even nowadays organic solvents are most often used in enteric coating processes. The evaporation of solvents and their possible harmful effects on tablet structure may, however, restrict the usability of the coating technique. Often plasticizers or some other components are mixed into the coating solution to improve film quality. Typical problems of enteric coating include tackiness, too porous structure or cracking of the films. Naturally, also all the other problems occasionally occurring in conventional film coating processes may exist in enteric coatings. The controlling and repeatability of the whole manufacturing chain is especially complicated. Often difficulties may arise due to breaking or inhomogeneity of a thin enteric coating film. As a consequence, the drug content can be released earlier than desired.

It is also known to prepare controlled release preparations by compressing formulations containing matrix forming excipients. Due to poor flowing, stickiness and smeary properties of enteric coating polymers, this method is very seldom used for preparation of enteric formulations. Direct compression of these substances without granulation in manufacturing scale is hardly possible.

Polymeric matrix formers with enteric properties, which can be processed by compressing, would be important in respect to time and energy saving as well as to better controlling of the whole manufacturing chain. The manufacture of enteric formulations using a compression process is in principle a simple and easily controllable process. If the direct compression process without granulation as a preprocess can be performed, it is possible to design even more simplified and better controllable manufacturing processes.

Several disadvantageous process factors, e.g. granulation, drying of granules, usage of organic solvents, can then be avoided.

In patent application PCT/FI95/00331 corresponding to U.S. patent application Ser. No. 08/374,430 filed Jan. 19, 1995, claiming priority from the Finnish patent application Ser. No. 942686 filed on Jun. 7, 1994, a composition comprising compacts of starch acetates and active ingredients is disclosed. Said composition is characterized by its modifiable properties. In said patent application PCT/FI95/00331 it is also disclosed how to make different kinds of compacts, which are best suited for a certain purpose, e.g. controlled or sustained release. The release of the active ingredient from said composition is however not pH dependent.

As described above there is especially a need of pharmaceutical pH dependent controlled release compositions or entero-compositions such as compacts, e.g. tablets, granules and pellets. Even if the need for such a composition is especially prominent for pharmaceutical applications, such as drugs and natural health products, pH dependent controlled release compositions can be applied for designing compositions to be used as fertilizers, herbicides, diagnostic reagents, etc., as well.

SUMMARY OF THE INVENTION

It has now been found that by compensating part of the acetate residues in the starch acetate of the composition described in patent application PCT/FI95/00331 by dicarboxylate acid residues, a new kind of pH dependent controlled release composition is obtained, which is especially suitable for enteric use. Accordingly, the composition of the present invention provides a compact for enteric use, which is far easier and more cost-effective to prepare than conventional pharmaceutical entero-compositions.

The composition is a compact consisting essentially of an active ingredient or active ingredients and starch acetate dicarboxylates as the main functional components.

The present invention is related to a composition for pH dependent controlled release of active ingredients, especially drugs and natural health products, but also fertilizers, herbicides, insecticides and diagnostic reagents. The composition is a compactible mixture of the active ingredient and starch molecules substituted with acetate and dicarboxylate residues. Succinate is the most preferred example of such dicarboxylate residues.

The starch molecules can have the acetate and dicarboxylate residues attached to the same starch molecule backbone or on separate starch molecule backbones.

Methods for preparing said starch acetate dicarboxylates by transesterification or mixing of starch acetates and starch dicarboxylates respectively are described in the present invention.

The present invention provides a compact for pH dependent controlled release or enteric use which is easy and cheap to prepare. By preparing compositions according to the present invention environmental pollution is diminished because the use of diluents detrimental to environment needed in the preparation of films surrounding conventional enteric compositions can be avoided.

THE BRIEF DESCRIPTION OF THE DRAWINGS

Figure 3:
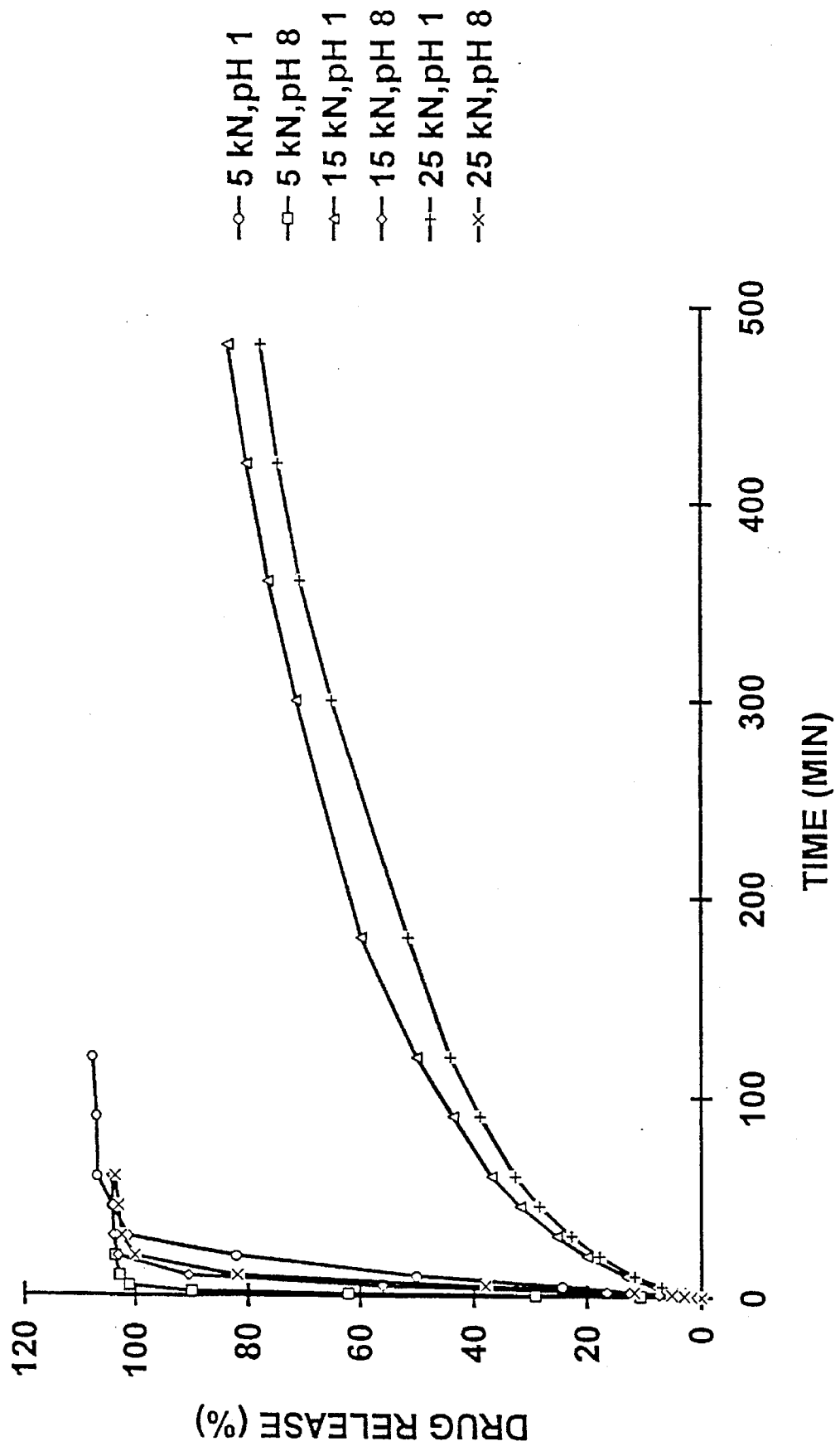

FIG. 3 depicts drug (anhydrous theophylline) release (%) as a function of time from tablets of starch acetate succinate. Tablets were prepared using three different compression forces. The pH of dissolution medium was 1 or 8.

Figure 4:
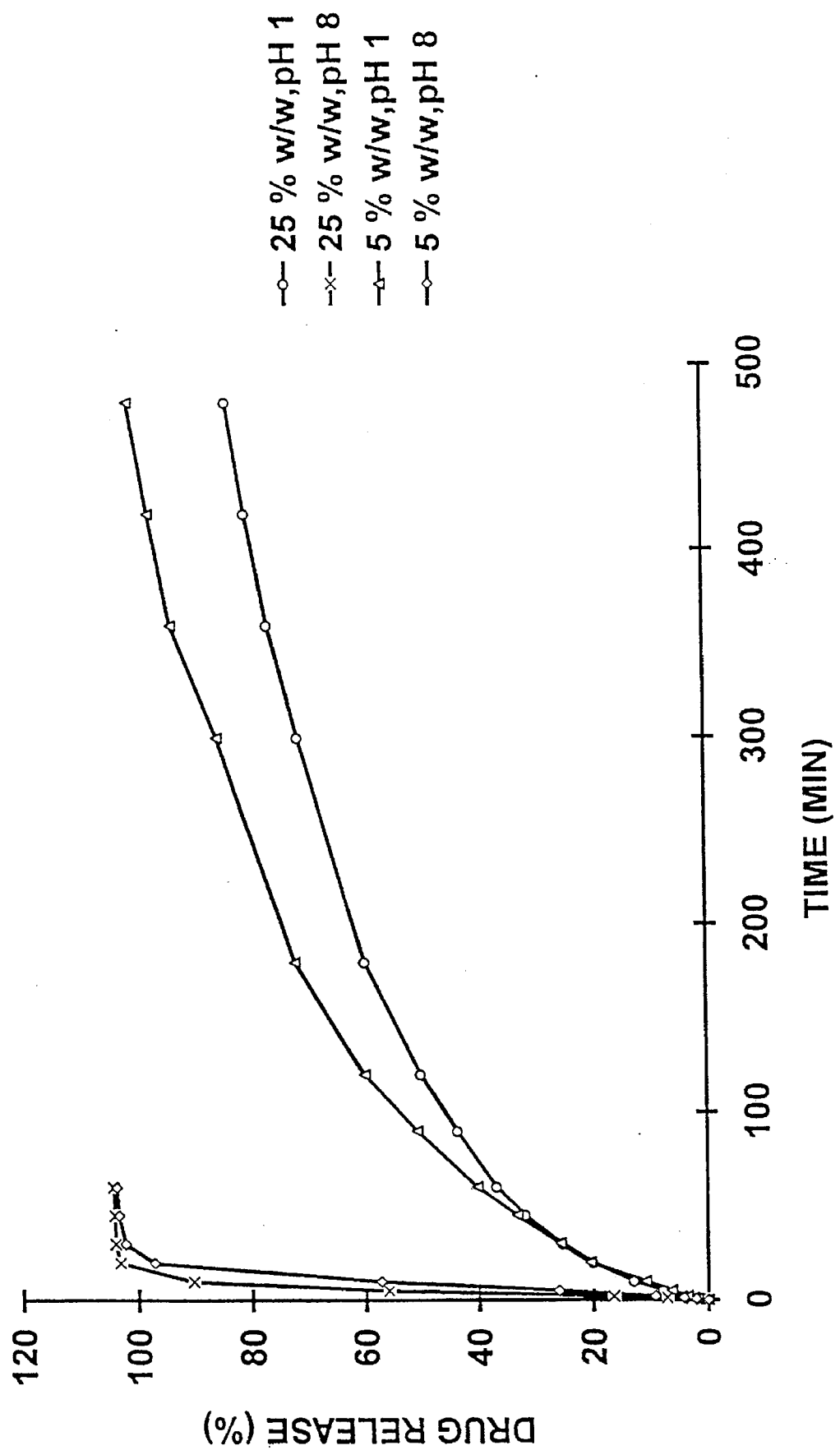

FIG. 4 depicts drug (anhydrous theophylline) release (%) as a function of time from starch acetate succinate tablets containing either 5 or 25% (w/w) of anhydrous theophylline. The pH of dissolution medium was 1 or 8.

Figure 5:
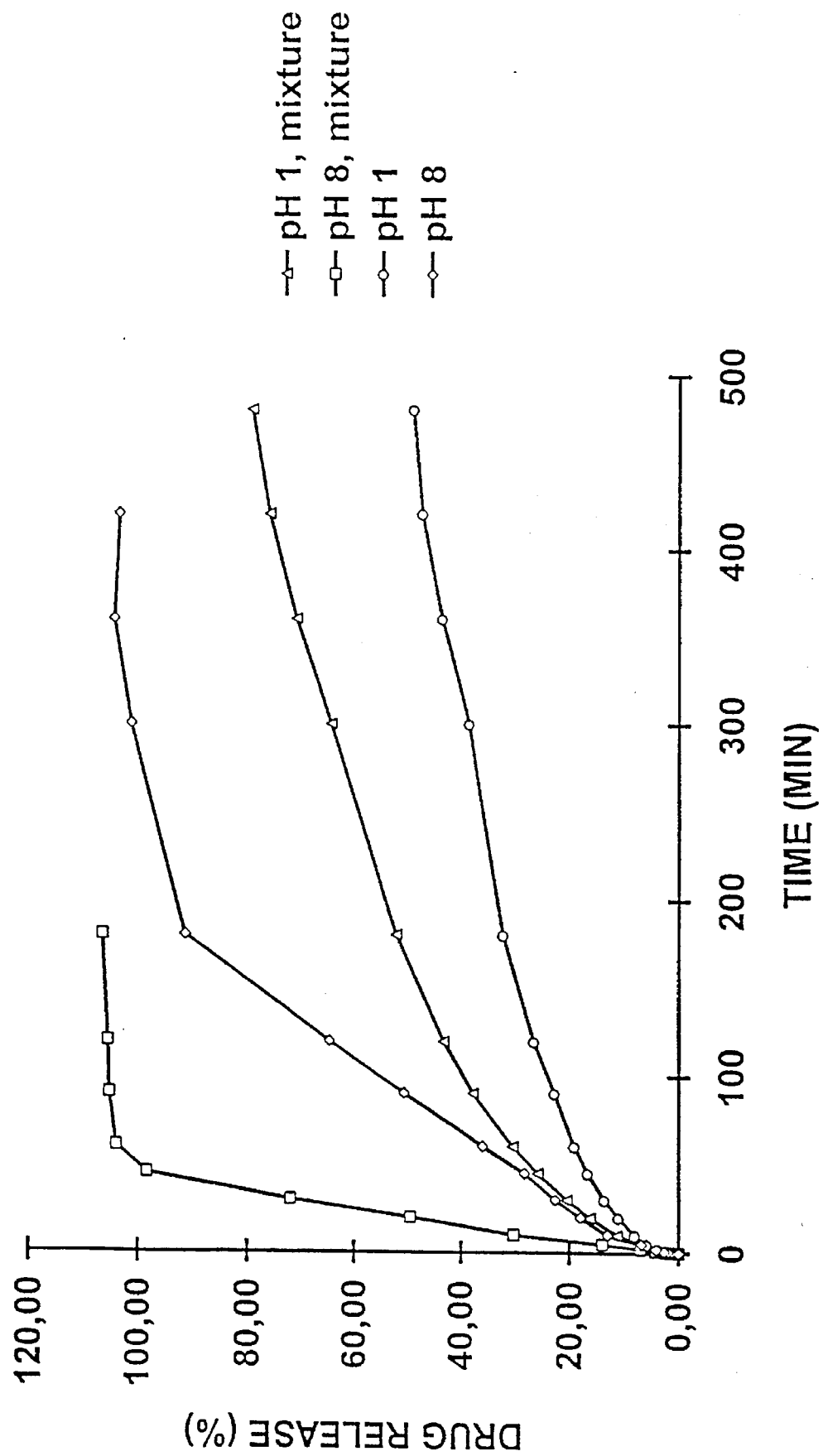

FIG. 5 depicts drug (anhydrous theophylline) release (%) as a function of time from starch acetate succinate tablets. Tablets contained starch acetate succinate either in the form of chemical compound of physical mixture. The pH of dissolution medium was 1 or 8.

Figure 6:
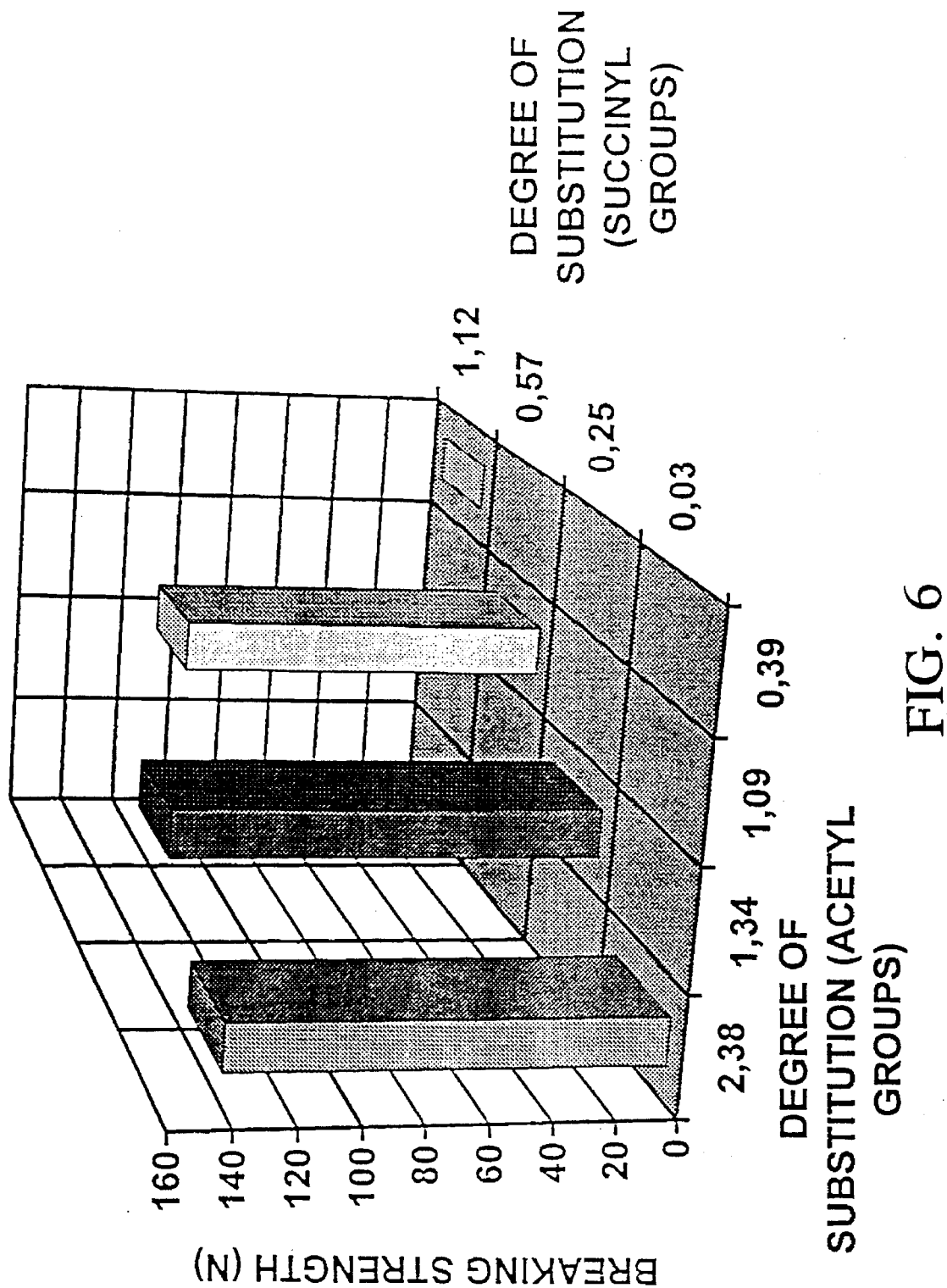

FIG. 6 depicts the mechanical strength measured as breaking strength values of tablets prepared of starch acetate succinate with different degrees of substitution.

Figure 7:
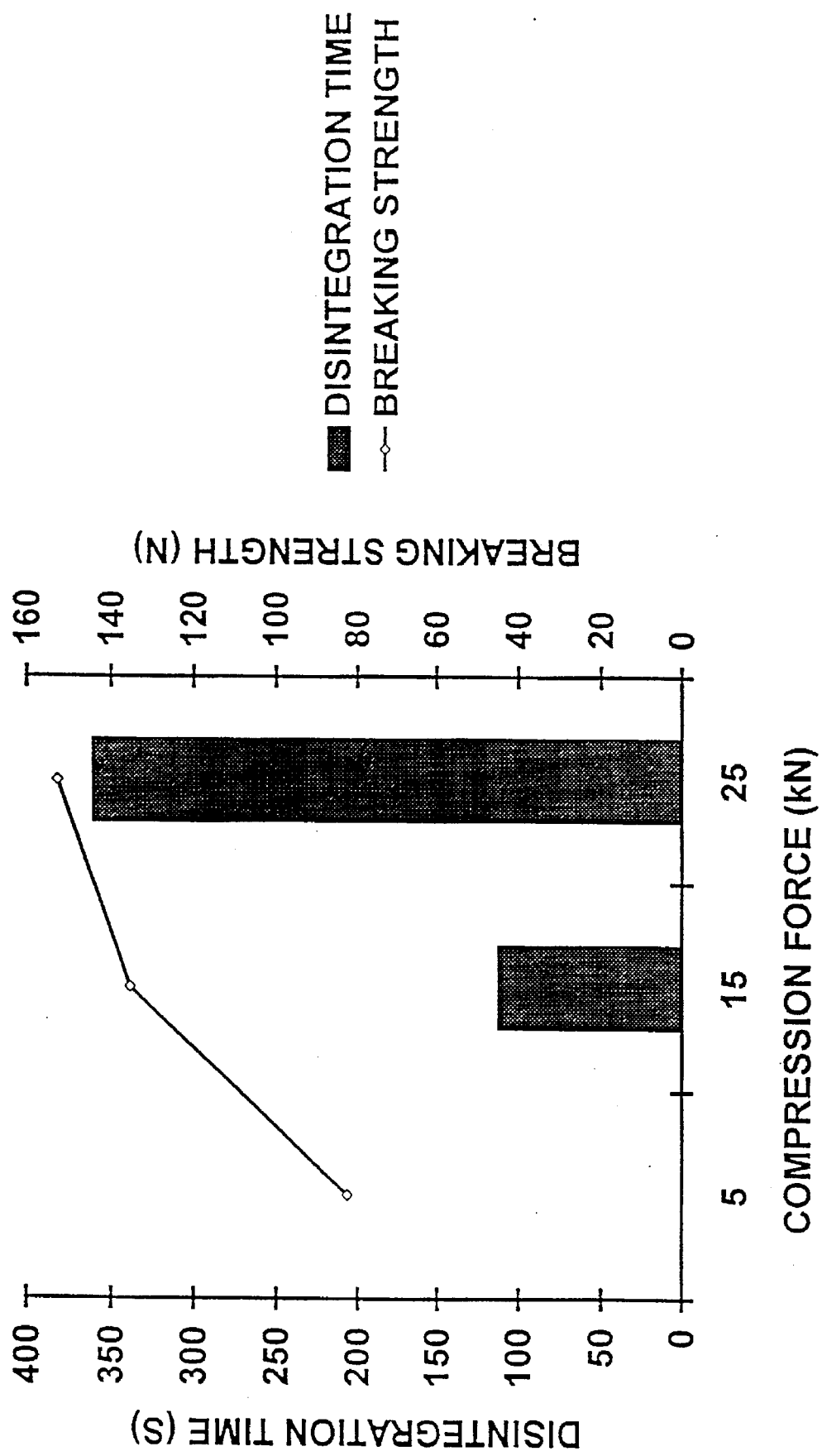

FIG. 7 depicts disintegration time in phosphate buffer (pH 6.8) and breaking strength of tablets of starch acetate succinate prepared using three different compression forces. Tablets, prepared using approximately 5 kN compression force, disintegrated already in 0.1N hydrochlorid acid, which was used as a disintegration medium during the first two hours of the disintegration test.

Figure 8A:
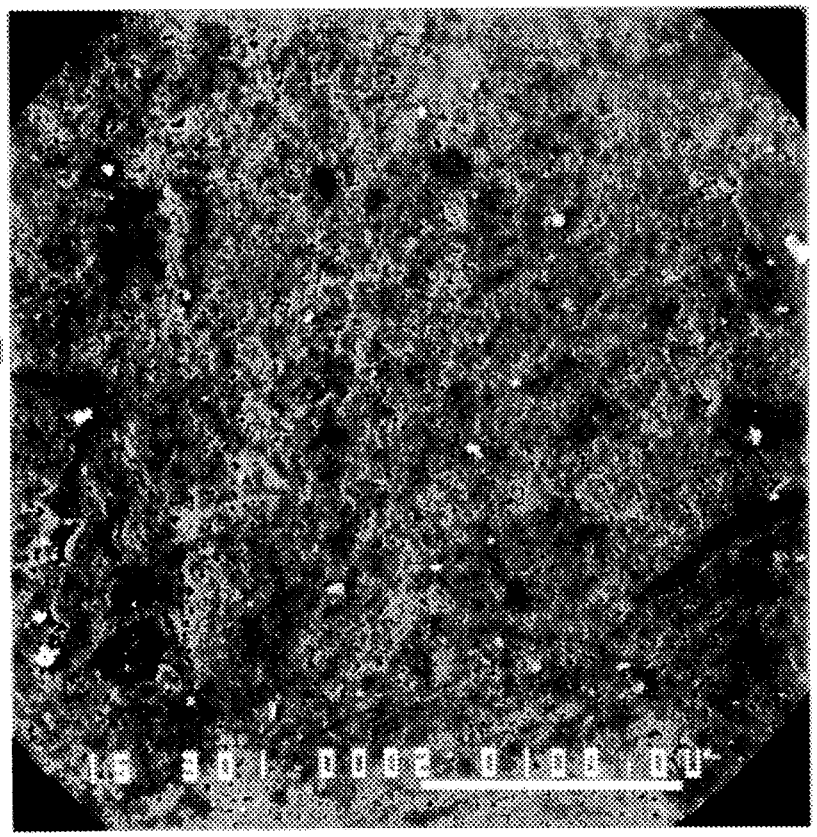

FIG. 8a depicts the surface of tablet of starch acetate succinate. The substitution degrees are 2.38 and 0.03 for acetyl and succinyl groups, respectively. The bar is 100 μm.

Figure 8B:
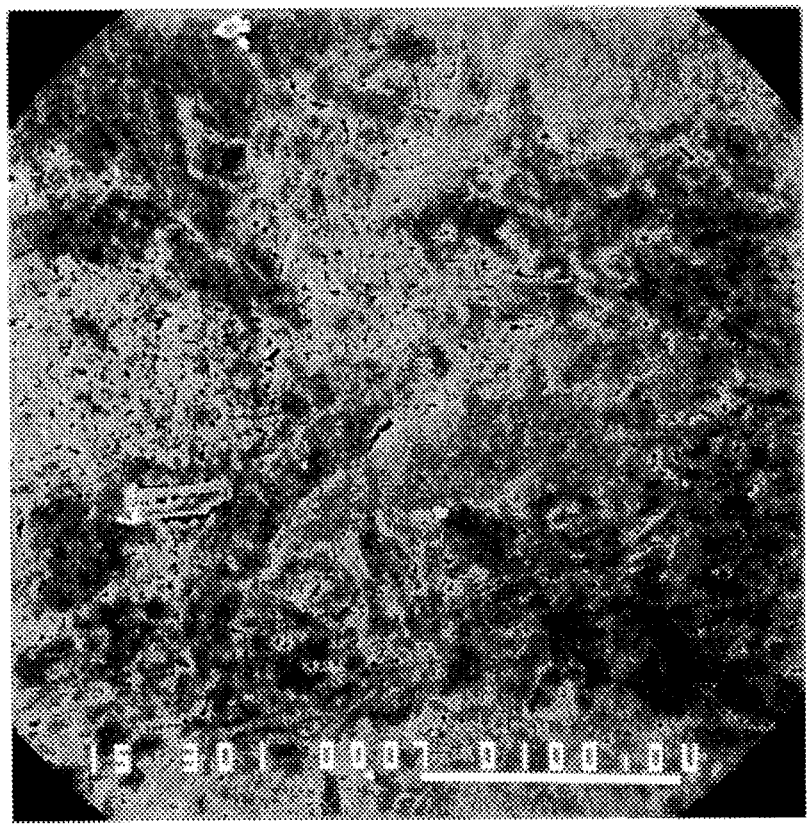

FIG. 8b depicts the surface of tablet of starch acetate succinate. The substitution degrees are 2.29 and 0.37 for acetyl and succinyl groups, respectively. The bar is 100 μm.

Figure 8C:
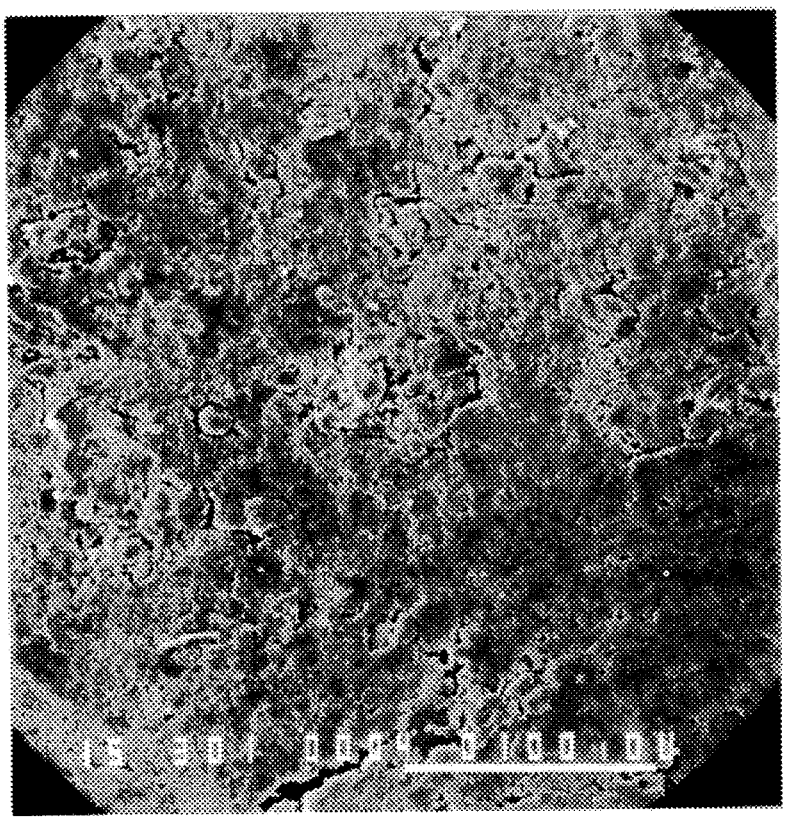

FIG. 8c depicts the surface of tablet of starch acetate succinate. The substitution degrees are 1.34 and 0.25 for acetyl and succinyl groups, respectively. The bar is 100 μm.

Figure 8D:
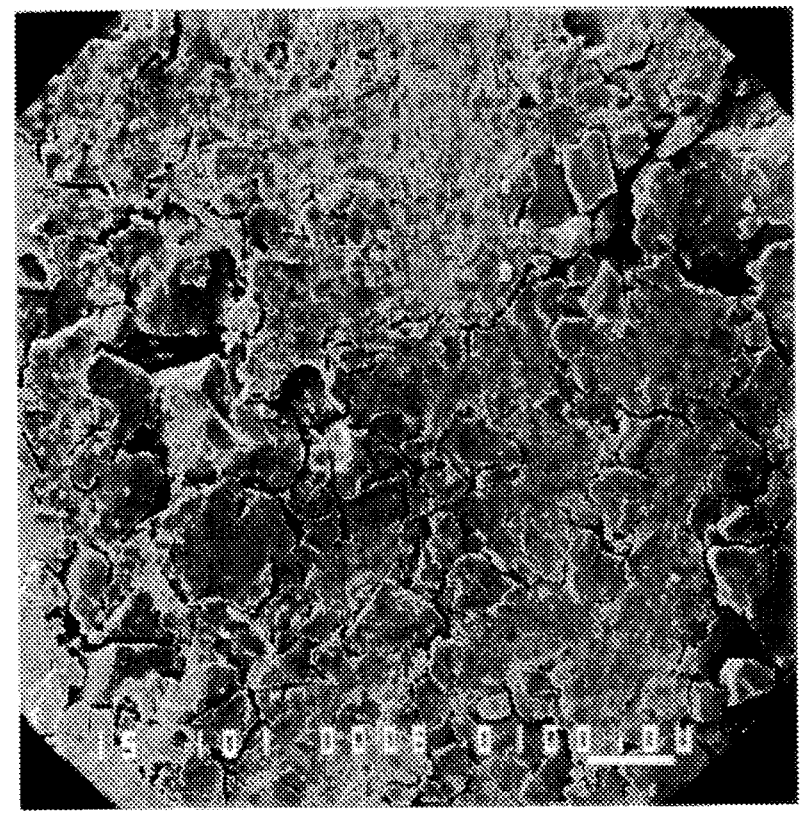

FIG. 8d depicts the surface of tablet of starch acetate succinate. The substitution degrees are 0.39 and 1.12 for acetyl and succinyl groups, respectively. The bar is 100 μm.

Figure 9A:
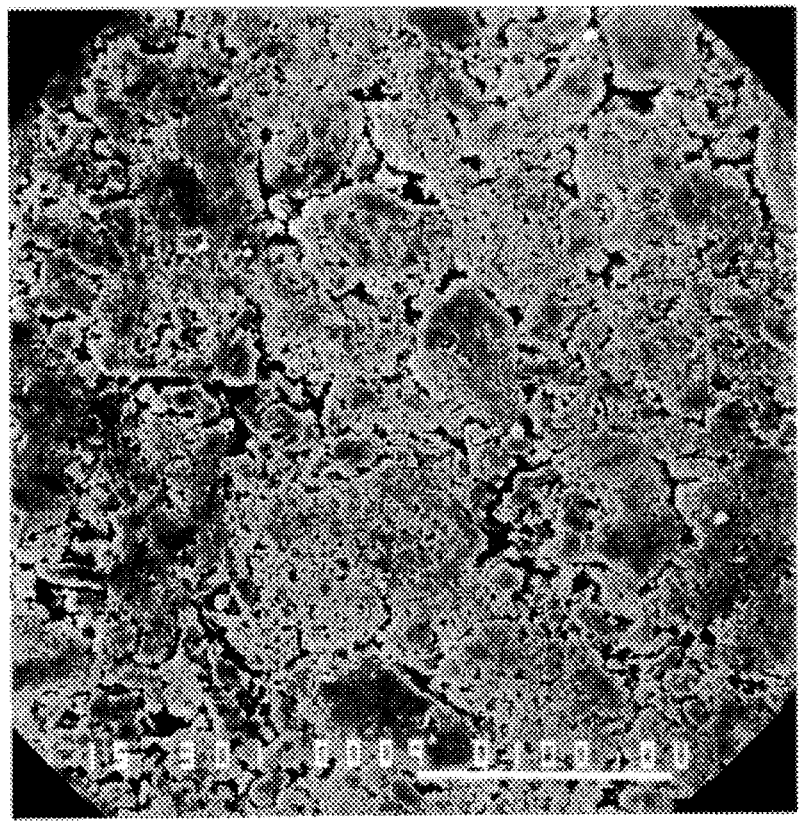

FIG. 9a depicts the surface of starch acetate succinate tablet compressed using approximately 5.7 kN force. The bar is 100 μm.

Figure 9B:
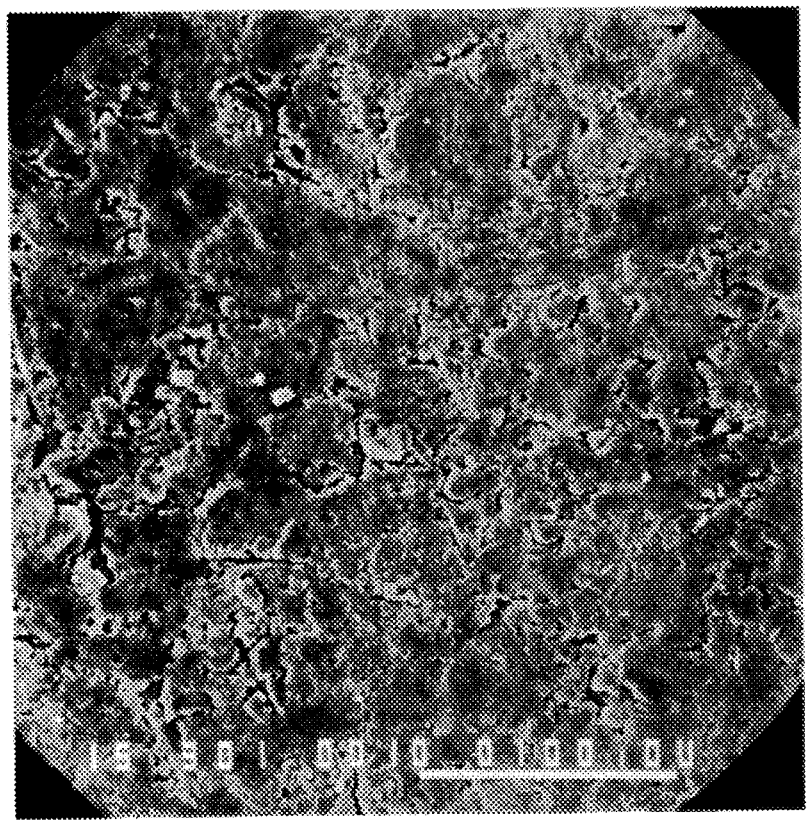

FIG. 9b depicts the surface of starch acetate succinate tablet compressed using approximately 15.3 kN force. The bar is 100 μm.

Figure 9C:
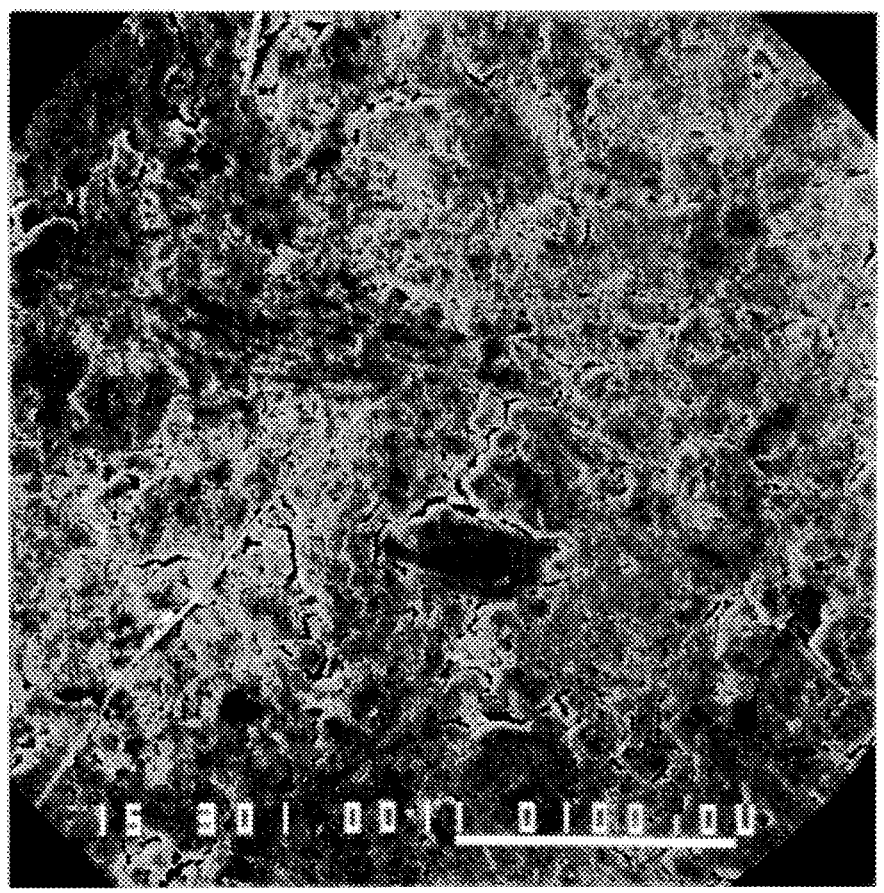

FIG. 9c depicts the surface of starch acetate succinate tablet compressed using approximately 25.2 kN force. The bar is 100 μm.

THE DETAILED DESCRIPTION OF THE INVENTION

In the following description, reference will be made to various methodologies known to those who are skilled in the art of starch chemistry and pharmaceutical technology. Publications and other materials describing the known methodologies are herewith incorporated in full.

General principles of starch chemistry are described for example in Modified Starch; Properties and Uses, Ed. Wurzburg, O. B., CRC Press Inc. , Boca Raton, Fla., 1986 and Starch; Chemistry and Technology, Eds. Whistler. R. C., BeMiller, J. N. and Paschall, E. F., Academic Press, Inc., Orlando, 1984.

General principles related to pharmaceutical technology are described for example in The Theory and Practice of Industrial Pharmacy 3rd Ed., Lachman, L., Lieherman, H. A: & Kanig; J. L. (EDs), Lea & Febiger, Philadelphia, 1986; and Pharmaceutical Dosage Forms: Tablets volume 1, 2, 3, Lieberman, H. A., Lachman, L. (EDs), Marcel Dekker Inc., New York, 1980.

General principles for pharmaceutical excipients are described for example in Martindale, The Extra Pharmacopeia, 30th Edition, The Pharmaceutical Press, London 1993 and Handbook of Pharmaceutical Excipients, 1994, American Pharmaceutical Association, The Pharmaceutical Society of Great Britain.

Definitions

Unless defined otherwise, all technical and scientific terms used herein have the same meaning as is commonly understood by one skilled in the art to which this invention belongs. In the description which follows a number of terms are extensively used. In order to provide a clear and consistent understanding of the specification and claims, including the scope to be given such terms, the following definitions are provided.

The term "composition" is intended to mean a compactible mixture, which comprises two groups of compounds i.e. at least one active ingredient and the starch derivative according to the present invention. They are principally developed for oral use for humans, including pharmaceutical enterotablets, compactible enterogranules or enteropellets. Also natural health products can be used as the active ingredient. The compositions can also be used in veterinary medicine or they can be used to carry herbicides, insecticides, fertilizers, diagnostic reagents, etc.

The term "active ingredient" is intended to mean drugs, medicines, vitamins, minerals, trace minerals, fibers, including glucan fibers, diagnostic reagents, herbicides, fertilizers, insecticides.

The term "natural health product" is used synonymously with the terms "natural health food products", "health food products" and "natural products" and is intended to mean products obtained from nature which are used in a medicine-like manner as health promoting, disease preventing products and/or otherwise beneficial food products, which do not necessarily have the authorization (approval) which is required for registered drugs. These substances include vitamins, minerals, trace minerals, antioxidants, fibers, etc.

The term "compactible" is intended to mean a mixture of the active ingredient and the starch derivative according to the present invention which, under the impact of compressing forces, forms compacts, such as tablets or other easily administrable dosage forms with sufficient breaking strength.

The term "compact" is intended to mean compressed tablets, compacted granules or pellets or other easily administrable dosage forms.

The term "starch" is intended to mean any form of starch, native or chemically or enzymatically hydrolyzed starch. Suitable starch is obtainable from barley, wheat, oats, corn, potato, tapioca, sago, rice and other tuber or grain based starch products, with an amylose content of 0–100% (w/w) and an amylopectin content of 100–0% (w/w). Especially preferred are starch products from barley and oats, which have an amylose content of 20–25% (w/w). In other words the molecular weight and amylose content of the starch is not a restricting factor for the starch used as starting material in the present invention.

The term "starch molecules substituted with acetate" is intended to mean that the starch molecules have been esterified with acetic acid or acetic anhydride or acetyl chloride and contain acetyl residues (synonymously used for groups or moieties), randomly distributed along the backbone of the starch molecule.

The term "starch molecules substituted with dicarboxylate" is intended to mean that the starch molecules have been esterified with preferably straight or branched chain dicarboxylic acids, straight or branched chain dicarboxylic anhydride or straight or branched chain dicarboxylic chloride or hydroxy dicarboxylic acid containing the corresponding acyl residues with different chain lengths such including oxalate, malonate, succinate, glutarate, adipate, pimelate, subcrate, azealate, sebacate, maleate, fumarate, realate, tartrate, citrate or mixtures of these dicarboxylates. The most preferred dicarboxylate acid is succinate. Some tricarboxylic acid including citrate are incorporated in the definition of the dicarboxylic acid as an example of branched chain dicarboxylic acids.

The term "starch molecules substituted with acetate and dicarboxylate residues" are intended to mean that they are starch molecules which are substituted by the residues defined above either on the same starch molecule backbone obtainable by e.g. transesterification methods or esterification with mixtures of reactive acetate or dicarboxylate groups. The term is also intended to mean that said substituents are present on different starch molecules which can be mixed in certain proportions in order to obtain the desired average substitution degrees.

The term "starch acetate succinate" is intended to mean that the acetyl and succinyl groups are on the same starch molecule backbone.

The term "starch molecules substituted with acetate and succinate" is intended to include both the starch acetate succinate and the starch molecule mixture which carries the acetyl and succinyl residues on separate starch molecule backbones.

An "average substitution degree (DS)" is intended to mean the actual substitution degree of the respective residues which are randomly distributed on starch molecules, which are substituted randomly by both residues or the average DS which can be calculated from the overall mixture which is obtainable when starch acetate with a certain DS is mixed with starch dicarboxylate with a certain DS in a certain ratio.

The term "controlled release" is intended to mean that the release of an active ingredient from a composition can be modified in a desired way.

The term "pH dependent controlled release of the active ingredient" is intended to mean that the rate of release is dependent of or regulated by the pH of the surrounding media or environment.

The term "retarded release" is intended to mean that the release is slower but not totally absent in acidic pH.

The term "enhanced release" is intended to mean that the release is more rapid in an essentially neutral or basic pH.

The term "essentially neutral pH" is intended to mean a pH 7 of about pH 5 up to pH 8. pH 8 is already defined as a basic solution.

The term "enterocomposition" is intended to mean that the controlled release of the active ingredient is pH dependent or pH regulated. The release of the active ingredient is retarded in an acidic solution and enhanced in an essentially neutral pH or basic pH.

The invention relates to a composition having properties especially useful for enteric use. The main characteristic of the invention is that using starch acetate dicarboxylate, as an essential excipient in compacts, pH dependent active ingredient release from the compositions or dosage forms can be achieved.

The composition for pH dependent controlled release of an active ingredient is essentially consisting of a compactible mixture of an active ingredient and starch molecules substituted with acetate and dicarboxylate residues. The dicarboxylate residues are selected from a group consisting of oxalate, malonate, succinate, glutarate, adipate, pimelate, suberate, azealate, sebacate, maleate, malate, fumarate, tartrate, citrate or mixtures of these dicarboxylates. The most preferred dicarboxylate acid is succinate. The same effect can be obtained also using a physical mixture of starch acetate and starch dicarboxylate instead of starch acetate dicarboxylate.

The starch molecules used in the composition have an average substitution degree of at least 1 for the acetate residue, but the higher the substitution degree is, the stronger tablets are obtained. Sufficiently strong tablets can be obtained with starch molecules could have an average substitution degree of at least 1.5 for the acetate residue. However, even stronger tablets are obtained, if the substitution degree of at least 2 is used for the acetate residue. Consequently, the starch molecules used in the composition advantageously have an average substitution degree between about 1.00–2.95 for the acetate residue.

The starch molecules used in the composition have an average substitution degree in the approximate range 0.05–1.5 for the dicarboxylate residue. Some pH dependent release can be detected with as small dicarboxylate substitution degrees as less than 0.05 but better results are achieved when an average substitution degree of 0.2–1.2 for the dicarboxylate residue is used. If the mechanical strength of the tablet is not a prerequisite property, the DS for acetate can be less than 1. By changing the DS of the acetate and dicarboxylate residues the functional properties of the tablet can be modified in desired ways.

The composition of the present invention is typically a compact, more specifically for pharmaceutical application it is either a tablet, granule or pellet. The composition can be designed as a single unit tablet or a multiple unit dosage form, e.g. a gelatin capsule filled with numerous enterogranules or enteropellets. The composition can be modified to be suitable for different uses by changing the substitution degrees, molar mass of the starch acetate succinate polymer, by changing the shares of physical mixture of starch acetate and succinate, by changing the drug amount and amount of other excipients in the formulation. It is also possible to modify the pH-dependent controlled release effect or entero-effect by using at least two different types of starch acetate dicarboxylate and by using different substitution degrees in these dicarboxylates. It is also possible to modify the entero-effect by using at least two different types of starch acetate succinates with different substitution degrees.

Essentially two types of starch can be used in the composition. The starch molecules can have the acetate and dicarboxylate residues attached to the same starch molecule backbone or the acetate and dicarboxylate residues can be on separate starch molecule backbones and combined as a physical mixture before compacting.

It is however possible to replace part of the starch molecules substituted with dicarboxylate and succinate residues, preferably about 20–50%, most preferably about 30–40%, with native starch or modified starch. It is however essential that the composition still contains such an amount of dicarboxylate residues that it fulfills the DS criteria according to the present invention. In the composition in which the acetate and dicarboxylate residues are on separate starch molecules, part or almost all, preferably 10–99%, most preferably 20–80% of the starch acetate can be replaced by native starch or more preferably modified starch. The replacing modified starch can for example be gelatinized or cross-linked starches as described in Predeepkumar, P. et al., Pharmaceutical Research, Vol. 10. (11), 1993.

The pharmaceutical, natural health product and diagnostic reagent compositions of the present invention is intended to be administered orally, but it is in no way excluded to use the invention to prepare compositions for other applications, including e.g. rectal compositions. The active ingredient in the formulation is not released in any essential degree from the composition in the acid environment of stomach, but fast release is achieved as soon as the composition reaches the neutral environment in small intestine. The entero-effect is due to the fast disintegration of the compact and possible also to partial dissolution of starch acetate dicarboxylate in neutral environment.

Because the composition is a compact, some minor release of the active ingredient can occur already in stomach. This is due to the release of the active ingredient from the outer surface of the compact. The amount of active ingredient released in this phase depends on the active ingredient concentration in formulation as well as the compression force used. The amount is typically clearly less than 30%. The rest of the active ingredients is released rapidly in small intestine. The biphasic release profile, consisting of a loading dose released in stomach and a maintaining dose released in small intestine, is beneficial especially in long lasting drug therapy for reaching the relatively steady drug concentrations in blood.

The composition can be prepared as essentially by four methods described below. These methods can be modified in several ways and there are several alternative methods which can be used in each step.

Alternative 1.

Starch acetate molecules are prepared by conventional methods. Part of the acetate residues in the starch acetate molecules are substituted with dicarboxylate residues using transesterification methods to obtain starch acetate dicarboxylate molecules in which the dicarboxylate residues can be any of those mentioned above. The most preferred being succinate residues.

Alternative 2.

Starch dicarboxylate molecules are prepared by conventional methods. Part of the dicarboxylate residues of the starch dicarboxylate molecules are substituted with acetate residues using transesterification methods to obtain starch acetate dicarboxylate molecules;

Alternative 3.

Starch acetate dicarboxylate molecules can be prepared by allowing a mixture of reactive acetyl and dicarboxyl groups to react with starch. These mixtures can include a mixture of acetic acid and dicarboxylic acid, acetyl and dicarboxyl anhydride, acetyl and dicarboxyl chloride, respectively. Compatible combinations of these mixtures and methods can also be used.

Alternative 4.

Starch acetate and starch dicarboxylate molecules are prepared separately by conventional methods. These two types of molecules are mixed together in desired ratios so that starch mixtures which have the desired properties—compactibility and pH dependent controlled release—are obtained. It is also possible to use instead of a single dicarboxylate starch, mixtures of different starch dicarboxylates.

Finally the starch acetate dicarboxylates obtained are mixed with one or more active ingredient(s) and the mixture is compressed essentially as described in the International patent application PCT/FI95/00331 which is hereby fully incorporated by reference, to obtain the compacts for pH dependent controlled release of the active ingredient.

Methods of preparing the starch acetate dicarboxylate molecules used in the present invention are described in more detail in the following examples, which should be read as describing the invention and not limiting the same. The preparation of the compacted compositions and their properties as well as test methods used are described in more detail in the experiments. The experiments should not be read to limit the scope of the present invention but to clarify the applicability of the invention.

EXAMPLE 1

The preparation of starch acetate succinate by transesterification

Starch acetate succinates were prepared by transesterification of starch acetate. The quantities of reagents and reaction conditions are shown in Table 1.

TABLE 1

The preparation of starch acetate succinates by transesterification and reaction conditions

| Batch | Starch acetate DS[1] | Starch acetate g | Pyridine g | Succinic anhydride g | Reaction conditions °C. | h |
|---|---|---|---|---|---|---|
| No. 1 | 2.84 | 70 | 250 | 45 | 85–90 | 6 |
| No. 2 | 2.84 | 70 | 150 | 45 | 85–90 | 16 |
| No. 3 | 3.0 | 13,9 | 50 | 8,8 | 85–90 | 16 |
| No. 4 | 1.7 | 70 | 500 | 175 | 85–90 | 12 |

[1]Analysis method of the degree of substitution: Wurzburg. O.B., Acetylation, In Methods in Carbohydrate Chemistry, Vol. IV, ed. R. L. Whistler, Academic Press, New York and London, 1964, p. 288.

Starch acetate succinates were prepared in flat flange reactor vessels made of glass with coil condenser, mechanical stirrer, thermometer and oil bath.

Starch acetate and pyridine were mixed for 30 minutes in 90° C. After mixing succinic anhydride was added to the reaction mixture for an hour. The reaction conditions used are illustrated in Table 1. After the reaction was completed, the mixture was cooled and precipitated from acidic solution with mechanical rapid stirring. After precipitation the pH value of the solution was 2–4. The precipitate was filtered and washed with water until pH value was over 5. In the end of the process the product was airdried. The results of the analyses of starch acetate succinates are illustrated in Table 2.

TABLE 2

Analyses of starch acetate succinates

| Batch | Degree of substitution DS[1] acetate | succinate | Dry content % | Ash % | Molecular weight g/mol[2] |
|---|---|---|---|---|---|
| No. 1 | 2.75 | 0.03 | 98.1 | 0.04 | Mw = 117300 Mn = 32170 |
| No. 2 | 2.38 | 0.03 | 95.4 | 0.27 | Mw = 117300 Mn = 32170 |

TABLE 2-continued

Analyses of starch acetate succinates

| Batch | Degree of substitution DS[1] acetate | succinate | Dry content % | Ash % | Molecular weight g/mol[2] |
|---|---|---|---|---|---|
| No. 3 | 2.29 | 0.13 | 97.6 | 0.13 | Mw = 117300 Mn = 32170 |
| No. 4 | 1.09 | 0.57 | 98.4 | 0.06 | Not measurable |

[1]Analysis method of the degree of substitution: Wurzburg. O.B., Acetylation, In Methods in Carbohydrate Chemistry, Vol. IV, ed. R. L. Whistler, Academic Press, New York and London, 1964, p. 288.
[2]GPC-analyses were made by Alko Group Ltd. Alcohol Control Laboratory (ACL) Equipment: HP-1090, two column in series (Waters, Ultra Hydrogel 2000), solvent 50 nM NaOH, temperature 40°C., dextran standards, RI- and viscosity-detectors. Only molecular weights of starting materials of starch acetate are measured.

EXAMPLE 2

The preparation of starch acetate succinate in organic solvent without transesterification The preparation of starch acetate succinate was also done without transesterification. The preparation was performed using both acetic anhydride and succinic anhydride in organic solvent. The quantities of reagents are illustrated in Table 3.

TABLE 3

The preparation of starch acetate succinates and reaction conditions

| Batch | Starch° g | Pyridine g | Acetic anhydride g | Succinic anhydride g | Reaction condition °C. | h |
|---|---|---|---|---|---|---|
| No. 5 | 70 | 250 | 112 | 43.2 | 85–90 | 3¹/6² |
| No. 6 | 70 | 150 | 112 | 43.2 | 105 | 3¹/6² |
| No. 7 | 125 | 250 | 250 | 125.0 | 85–90 | 3¹/6² |
| No. 8 | 125 | 250 | 250 | 125.0 | 85–90 | 1³/4² |

°Hydrolyzed barley starch
[1]Reaction time for acetylation
[2]Reaction time for the whole reaction
[3]Reaction time for succinylation Starch acetate succinates were prepared with the reaction equipment described in Example 1.

Starch acetate and pyridine were mixed for 30 minutes in 90° C. In Batch No. 5, 6 and 7 acetic anhydride and in Batch No. 8 succinic anhydride was added to the mixture and the reaction was performed using the reaction conditions illustrated in Table 3. In Batch No. 5, 6 and 7 succinic anhydride and in Batch No. 8 acetic anhydride was added and reaction was performed using the reaction conditions illustrated in Table 3. After the reaction was completed, the mixture was cooled and precipitated from acidic solution with mechanical, rapid stirring. After precipitation the pH value of the solution was succinates are illustrated in Table 4.

TABLE 4

Analyses of starch acetate succinates

| Batch | Degree of substitution DS[1] acetate | succinate | Dry content % | Ash % | Molecular weight g/mol[2] |
|---|---|---|---|---|---|
| No. 5 | 1.51 | 0.15 | 98.1 | 0.29 | Mw = 117300<br>Mn = 32170 |
| No. 6 | 1.34 | 0.25 | 98.7 | 0.37 | Mw = 117300<br>Mn = 32170 |
| No. 7 | 1.83 | 0.09 | 98.1 | 0.13 | Mw = 117300<br>Mn = 32170 |
| No. 8 | 0.39 | 1.12 | 95.8 | 0.17 | Mw = 117300<br>Mn = 32170 |

[1]Analysis method of the degree of substitution: Wurzburg. O.B., Acetylation, In Methods in Carbohydrate Chemistry, Vol. IV, ed. R. L. Whistler, Academic Press, New York and London, 1964, p. 288.
[2]GPC-analyses were made by Alko Group Ltd. Alcohol Control Laboratory (ACL) Equipment: HP-1090, two column in series (Waters, Ultra Hydrogel 2000), solvent 50 nM NaOH, temperature 40°C., dextran standards, RI- and viscosity-detectors. Molecular weights of starch are only measured.

EXAMPLE 3

The preparation of starch acetate in acetic anhydride

Starch acetate was prepared in acetic anhydride using sodium hydroxide as reaction catalyst. The quantities of reagents and reaction conditions are shown in Table 5.

TABLE 5

The preparation of starch acetate and reaction conditions

| Batch | Starch[1] kg | Acetic anhydride kg | Sodium hydroxide kg | Reaction conditions °C. | h |
|---|---|---|---|---|---|
| No. 9 | 37.5 | 150 | 8.25 | 125 | 5 |

[1]Hydrolyzed barley starch

Starch acetate was prepared in 300 dm³ reactor with mechanical stirrer and oil heating. Starch and acetic anhydride were mixed in 45° C. Sodium hydroxide was added to the reaction mixture for 10 minutes. Heating was increased and reaction was allowed to occur using the reaction conditions illustrated in Table 5. After the reaction was completed, the mixture was cooled, precipitated from water, washed and dried. The results of the analysis of starch acetate is illustrated in Table 6.

TABLE 6

Analysis of starch acetate

| Batch | Degree of substitution DS[1] | Dry content % | Ash % | Molecular weight g/mol[2] |
|---|---|---|---|---|
| No. 9 | 2.76 | 83.4 | 0.11 | Mw = 117300<br>Mn = 32170 |

[1] and [2] compare with Table 4

EXAMPLE 4

The preparation of starch succinate in organic solvent

Starch succinate was prepared in organic solvent with quantities of reagents and reaction conditions shown in Table 7.

TABLE 7

The preparation of starch succinate and reaction conditions

| Batch | Starch[1] g | Succinic anhydride g | Pyridine g | Dimethyl formamide g | Reaction conditions °C. | h |
|---|---|---|---|---|---|---|
| No. 10 | 150 | 290 | 180 | 500 | 80–85 | 7 |

[1]Hydrolyzed barley starch

Starch succinate was prepared with the reaction equipment described in Example 1 as described below. The results are shown in Table 8.

TABLE 8

Analysis of starch succinate

| Batch | Degree of substitution DS[1] | Dry content % | Ash % | Molecular weight g/mol[2] |
|---|---|---|---|---|
| No. 10 | 1.7 | 96.2 | 0.14 | Mw = 117300<br>Mn = 32170 |

[1] and [2] compare with Table 4.

Starch and pyridine were mixed and refluxed for 90 minutes in 90° C. Part of dimethylformamide was added to the reaction mixture and the rest of it was mixed with succinic anhydride and they were added together to the mixture. After reaction the mixture was dissolved to sodium bicarbonate solution and ultrafiltered. The results of the analysis of starch succinate is illustrated in Table 8.

EXAMPLE 5

The physical mixture of starch acetate and starch succinate

The physical mixture was made from starch acetate and starch succinate. The preparation of these starch acetate and succinates are described in Batches 3 and 4, Batch No. 9 and 10. In the Table 9 the degrees of substitution of starch acetate and starch succinate and the average degrees of substitution of acetyl residues and succinyl residues in the physical mixture are shown.

TABLE 9

The degrees of substitution of starch acetate and starch succinate and the average degrees of substitution of acetyl residues and succinyl residues in the physical mixture.

| Batch | Starch acetate DS | Starch succinate DS | Physical mixture w/w | Acetate DS[1] | Succinate DS[1] |
|---|---|---|---|---|---|
| No. 11 | 2.76 | 1.7 | 1:1 | 1.56 | 0.76 |

[1]in mixture (average)

EXAMPLE 6

The preparation of starch acetate succinate in glacial acetic acid

The preparation of starch acetate succinate was also performed using glacial acetic acid as intermediate agent. The quantities of reagents are illustrated in Table 10.

TABLE 10

The preparation of starch acetate succinate and reaction conditions

| Batch | Starch[1] g | Glacial acetic acid g | Acetic anhydride g | Succinic anhydride g | NaOH g | Reaction condition °C. | h |
|---|---|---|---|---|---|---|---|
| No. 12 | 50 | 350 | 94.4 | 61.7 | 11 | 85–90<br>110–115 | 3[2]<br>3[3] |
| No. 13 | 50 | 250 | 126 | 61.7 | 11 | 85–90 | 2 |

[1] Hydrolyzed barley starch
[2] Reaction conditions for succinylation
[3] Reaction conditions for the acetylation Starch acetate succinates were prepared with the reaction equipment described in Example 1.

Starch and glacial acetic acid were mixed for 30 minutes in 45°–50° C. In Batch No. 12 succinic anhydride and in Batch No. 13 both succinic anhydride and acetic anhydride was added to mixture. After 15 minutes sodium hydroxide was added drop by drop and reaction was allowed to occur in the reaction conditions illustrated in Table 3. After the reaction had happened in Batch No. 12 acetic anhydride was added and reaction was done with reaction conditions illustrated in Table 3.

After the reaction was completed the mixture was cooled and excess acetic acid was distilled in vacuum. After distillation the mixture was precipitated from water with mechanical rapid stirring, filtered, washed and dried. The results of the analyses of starch acetate succinates are illustrated in Table 11.

TABLE 11

Analyses of starch acetate succinates

| Batch | Degree of substitution DS[1] acetate | Degree of substitution DS[1] succinate | Dry content % | Ash % | Molecular weight g/mol[2] |
|---|---|---|---|---|---|
| No. 12 | 0.18 | 1.36 | 95.6 | 0.06 | Mw = 117300<br>Mn = 32170 |
| No. 6 | 0.16 | 0.69 | 98.3 | 0.97 | Mw = 117300<br>Mn = 32170 |

[1] and [2] compare with Table 4.

EXAMPLE 7

The preparation of starch acetate succinate in glacial acetic acid by transesterification The preparation of starch acetate succinate was also performed by transesterification of starch acetate using glacial acetic acid as inert agent. Sodium hydroxide and sodium acetate were used as transesterification catalysts.

The quantities of reagents are illustrated in Table 12.

TABLE 12

The preparation of starch acetate succinate and reaction conditions

| Batch | Starch acetate DS | Starch acetate g | Glacial acetic g | Succinic anhydride g | Catalyst g | Reaction conditions °C. | h |
|---|---|---|---|---|---|---|---|
| No. 14 | 3.0 | 70 | 245 | 73 | 19[1] | 85–90 | 6 |
| No. 15 | 3.0 | 50 | 400 | 92.6 | 22[2] | 85–90 | 3 |

[1] Sodium hydroxide
[2] Sodium acetate

Starch acetate succinates were prepared with the reaction equipment described in Example 1.

Starch acetate and glacial acetic acid were mixed for 30 minutes in 45°–50° C. and succinic anhydride was added to the mixture. After 15 minutes the transesterification catalyst, in Batch No. 14 sodium hydroxide and in Batch No. 15 sodium acetate, was added drop by drop and the reaction was allowed to happen in the reaction conditions illustrated in Table 3. When the reaction was completed, the mixture was cooled and excess acetic acid was distilled in vacuum. After distillation the mixture was precipitated from water with mechanical, rapid stirring, filtered, washed and dried. The results of the analyses of starch acetate succinates are illustrated in Table 13.

TABLE 13

Analyses of starch acetate succinates

| Batch | Degree of substitution acetate DS[1] | Degree of substitution succinate DS[1] | Dry content % | Ash % | Molecular weight g/mol[2] |
|---|---|---|---|---|---|
| No. 14 | 2.35 | 0.10 | 99.0 | 0.05 | Mw = 117300<br>Mn = 32170 |
| No. 15 | 2.90 | 0.10 | 99.2 | 0.17 | Mw = 117300<br>Mn = 32170 |

[1] and [2] compare with Table 4.

EXAMPLE 8

The preparation of starch acetate succinate in acetic anhydride

The preparation of starch acetate succinate was also done by using acetic anhydride both as reagent and intermediate agent for the reaction. Sodium hydroxide was used as reaction catalysts. The quantities of reagents are illustrated in Table 14.

Starch acetate succinates were prepared with the reaction equipment described in Example 1.

Starch and acetic anhydride were mixed for 30 minutes in 45°–50° C. and sodium hydroxide was added to the mixture drop by drop and the reaction was allowed to occur using the reaction conditions illustrated in Table 14. After the acetylation reaction had occured the succinic anhydride was added to the mixture and the reaction was allowed to occur in the reaction conditions illustrated in Table 14.

TABLE 14

The preparation of starch acetate succinates and reaction conditions

| Batch | Starch[1] g | Acetic anhydride g | Succinic anhydride g | NaOH g | Reaction conditions °C. | h |
|---|---|---|---|---|---|---|
| No. 16 | 50 | 200 | 46.3 | 11 | 120–125<br>85–90 | $3^2$<br>$3^3$ |
| No. 17 | 50 | 200 | 61.7 | 11 | 120–125<br>85–90 | $2^2$<br>$4^3$ |

[1] Hydrolyzed barley starch
[2] Reaction conditions for acetylation
[3] Reaction conditions for succinylation

TABLE 15

Analyses of starch acetate succinates

| | Degree of substitution | | Dry | | Molecular |
|---|---|---|---|---|---|
| Batch | acetate DS[1] | succinate DS[1] | content % | Ash % | weight g/mol[2] |
| No. 16 | 2.30 | 0.10 | 98.4 | 0.11 | Mw = 117300<br>Mn = 32170 |
| No. 17 | 1.78 | 0.10 | 97.7 | 0.20 | Mw = 117300<br>Mn = 32170 |

[1] and [2] compare with Table 4.

After the succinylation reaction the reaction mixture was cooled, precipitated from water with mechanical, rapid stirring, filtered, washed and dried. The results of the analyses of starch acetate succinates are illustrated in Table 15.

EXAMPLE 9

The preparation of starch acetate dicarboxylates

The preparation of starch acetate dicarboxylates starch acetate adipate and starch acetate sebacate were performed by using acetic anhydride both as reagent and intermediate agent for the reaction. Sodium hydroxide was used as reaction catalysts. The quantities of reagents are illustrated in Table 16.

TABLE 16

The preparation of starch acetate dicarboxylates and reaction conditions

| Batch | Starch[1] g | Acetic anhydride g | Dicarbocylic acid g | NaOH g | Reaction condition °C. | h |
|---|---|---|---|---|---|---|
| No. 18 | 50 | 200 | 45.1[4] | 11 | 120–125<br>130–135 | $3^2$<br>$2^3$ |
| No. 19 | 50 | 200 | 45.7[5] | 11 | 120–125<br>130–135 | $2^2$<br>$2^3$ |

[1] Hydrolyzed barley starch
[2] Reaction conditions for acetylation
[3] Reaction conditions for dicarboxylation
[4] Adipic acid
[5] Sebacic acid Starch acetate dicarboxylates were prepared with the reaction equipment described in Example 1.

Starch and acetic anhydride were mixed for 30 minutes in 45°–50° C. and sodium hydroxide was added to the mixture drop by drop and the reaction was allowed to occur using the reaction conditions illustrated in Table 16. After the acetylation reaction dicarboxylic acid was added to the mixture and the reaction was performed using the reaction conditions illustrated in Table 16. After the dicarboxylation reaction the reaction mixture was cooled, precipitated from water with mechanical, rapid stirring, filtered, washed and dried. The results of the analyses of starch acetate dicarboxylates are illustrated in Table 17.

TABLE 17

Analyses of starch acetate dicarboxylates

| | Degree of substitution | | Dry | | Molecular |
|---|---|---|---|---|---|
| Batch | acetate DS[1] | succinate DS[1] | content % | Ash % | weight g/mol[2] |
| No. 18 | 2.0 | 0.1 | 95.8 | 0.14 | Mw = 117300<br>Mn = 32170 |
| No. 19 | 2.7 | 0.1 | 97.4 | 0.81 | Mw = 117300<br>Mn = 32170 |

[1] and [2] compare with Table 4.

EXPERIMENT 1

The preparation of tablets

Tablets, containing starch acetate succinate, anhydrous theophylline as an active substance and magnesium stearate as a lubricant, were compressed using an instrumented eccentric tablet press (Korsch, EK-0, Berlin, Germany) and flat-faced punches with a diameter of 1 cm. The rate of the tablet press was 30 rpm. Before compression all powders were stored at 33% relative humidity and room temperature. Pre-weighed powder samples were poured manually into the die cavity and compressed to form tablets using compression force of 15 kN. In some experiments compression force was adjusted to 5 kN or 25 kN.

EXPERIMENT 2

Dissolution testing

The release of active substance, i.e. anhydrous theophylline, from starch acetate succinate tablets was determined using the USP (XXIII) rotating basket method at the rotation speed of 100 rpm. The volume of 300 ml of phosphate buffer with different pH value was used as dissolution medium. The concentration of phosphate buffer was 40 mM. Samples of 3 ml were withdrawn from the vessels at selected intervals, filtered through 0.2 μm membrane filters, suitably diluted with phosphate buffer solution. The experiments were accomplished for eight hours in maximum. The concentration of anhydrous theophylline was measured spectrophotometrically at a wavelength of 270 nm (Hitachi-220, Tokyo, Japan).

EXPERIMENT 3

The effect of pH of dissolution medium on drug release

Figure 1:
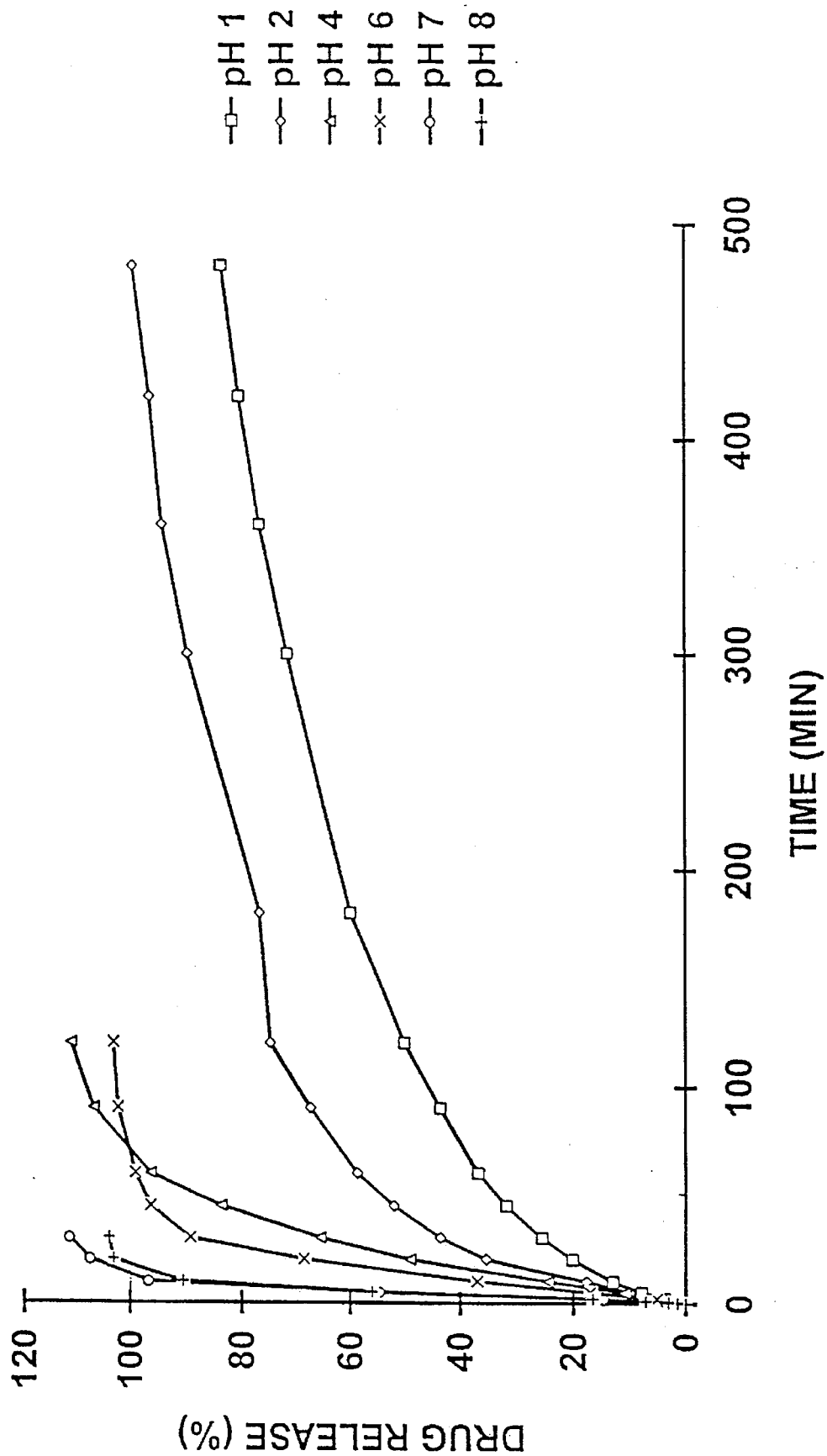
FIG. 1 depicts drug (anhydrous theophylline) release (%) as a function of time for tablets of starch acetate succinate. The pH of dissolution medium was 1, 2, 4, 6, 7 or 8.

The rate of drug release from matrix tablets was determined using phosphate buffers of various pH values as dissolution media is shown in FIG. 1. Tablets consisting of 74.5% (w/w) starch acetate succinate, 25% (w/w) anhydrous theophylline and 0.5% (w/w) magnesium stearate were prepared according to the method depicted in Example 1. The degrees of substitution were 1.34 and 0.25 for acetyl and succinyl groups, respectively. pH values of buffer solutions were 1, 2, 4, 6, 7 and 8.

The rate of drug release was delayed with decreasing pH value of dissolution medium. Both in basic, i.e. pH 8, and neutral, i.e. pH 7, medium anhydrous theophylline released completely in twenty minutes. In slightly acidic solution, i.e. pH 6 and 4, about 90 minutes was required to achieve complete drug release. Nevertheless, the rate of drug release was somewhat faster at pH 6 than pH 4 indicating pH dependent behaviour of starch acetate succinate. Drug release profiles at pH 2 and pH 1 were distinctly different compare to profiles obtained in basic, neutral or slightly acidic media. After eight hours of experiment about 99% and 83% of drug content of tablets was released at pH 2 and pH 1, respectively.

The behaviour of starch acetate succinate was definitely pH dependent, which was an advantageous property in the field of controlled drug delivery.

EXPERIMENT 4

The effect of degrees of substitution of starch acetate succinate on drug release Drug release from tablets, containing differently substituted starch acetate succinate as a matrix forming substance, was examined using the previously described method (Experiment 2). Anhydrous theophylline content in each tablet was 25% (w/w). The degrees of substitution of starch acetate succinate polymer are shown in Table 18. Dissolution studies were performed in basic, i.e. pH 8, and in acidic, i.e. pH 1, phosphate buffer solutions.

Figure 2:
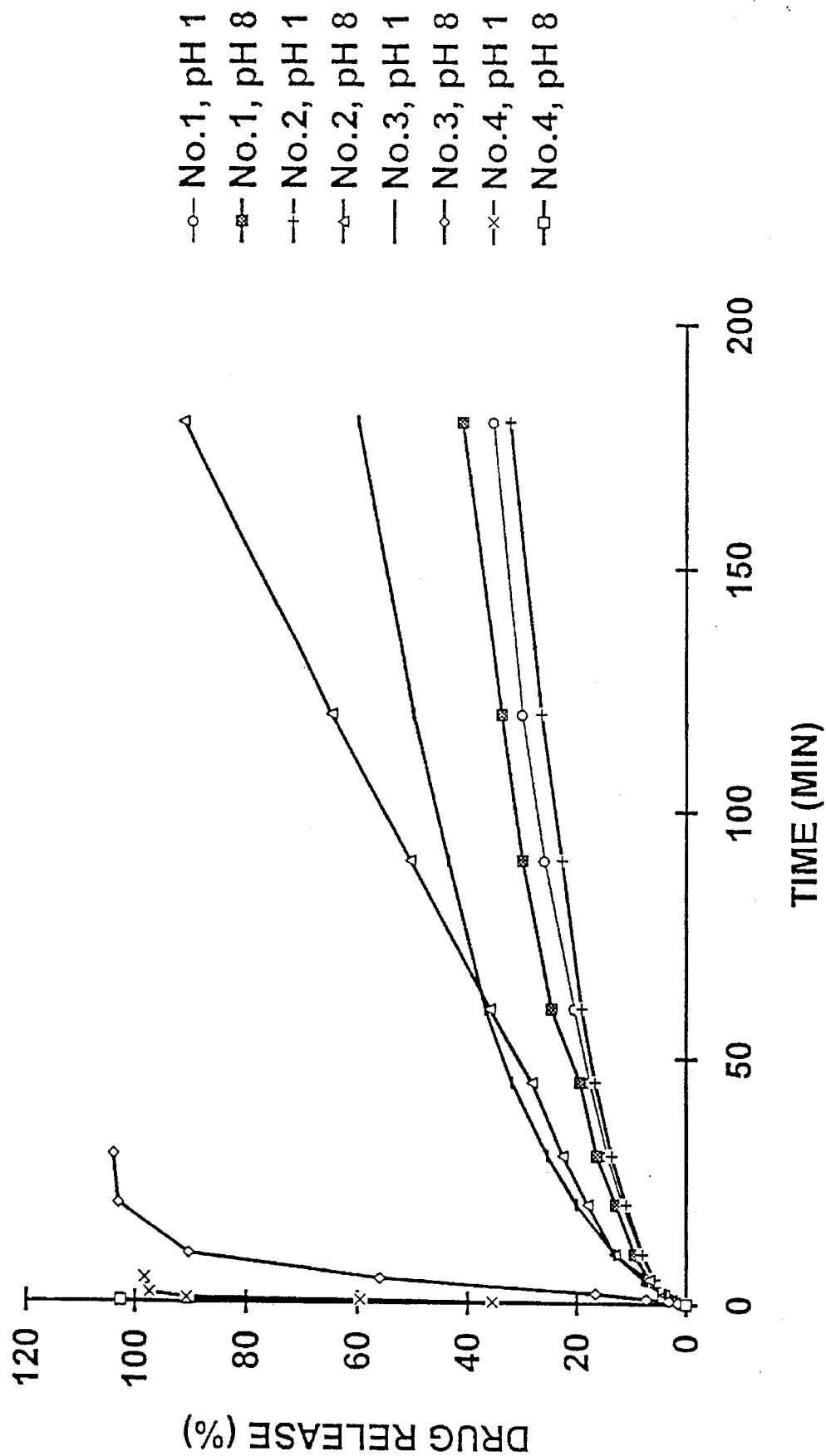
FIG. 2 depicts drug (anhydrous theophylline) release (%) as a function of time for tablets of starch acetate succinate with different degrees of substitution. The pH dissolution medium was 1 or 8.

As the starch molecule was highly substituted with acetyl groups, i.e. DS was above two, the release rate of active substance was slow, particularly in acidic environment (FIG. 2).

Drug release was slow also in basic solution as starch acetate succinate No. 1 was used to form matrix. Delayed release was probably due to the fairly small amount of succinyl groups, which was not sufficient enough to ensure rapid drug release in basic medium. In the case of starch acetate succinate No. 2, the succinyl content of polymer was distinctly higher when compared to polymer No. 1. Thus, the rate of drug release at pH 8 accelerated (FIG. 2).

TABLE 18

The degrees of substitution (DS) of acetyl and succinyl groups of different starch acetate succinate

| Starch acetate succinate | Acetate DS | Succinate DS |
| --- | --- | --- |
| No. 2 (Example 1) | 2.38 | 0.03 |
| No. 3 (Example 1) | 2.29 | 0.37 |
| No. 6 (Example 2) | 1.34 | 0.25 |
| No. 8 (Example 2) | 0.39 | 1.12 |

As the degree of substitution for acetyl groups was below 2.0 and the corresponding value on behalf of succinyl groups was underneath 1.0 (polymer No. 3) release of active substance was fast in basic solution (FIG. 2). However, the release rate was relatively slow at pH 1. Polymers, with that kind of pH dependent behavior, could be beneficial in many applications for controlled drug delivery.

Drug release from tablets composed of polymer No. 4, was very rapid in both media (FIG. 2). Acetyl contents of polymer is possibly too low to form proper matrix tablets. Besides low acetyl contents, the degree of substitution of polymer for succinyl groups was above one, which had an influence on the release rate of active substance, at least in basic solution.

By substituting starch molecule with acetyl and succinyl groups, polymer with pH dependent behaviour was achieved. It is possible to affect the rate of drug release by varying the amounts of acetyl and succinyl groups attached to the starch molecule.

EXPERIMENT 5

The effect of compression force on the rate of drug release from the starch acetate succinate tablets Three different compression forces, i.e. 5 kN, 15 kN and 2 kN, were used to prepare tablets composed of 74.5% (w/w) starch acetate succinate, 25% (w/w) anhydrous theophylline and 0.5% (w/w) magnesium stearate. The degrees of substitution for the starch acetate succinate polymer were 1.34 and 0.25 for acetyl and succinyl groups, respectively. The rate of drug release was examined in acidic, i.e. pH 1, and in basic, i.e. pH 8, phosphate buffer solution with the procedure as described previously (Experiment 2).

Regardless of pH of dissolution solution, the active substance released relatively rapidly from the tablets compressed at the lowest force, i.e. 5 kN (FIG. 3). The complete drug release was attained in five minutes as basic buffer solution was used. In acidic medium, the entire anhydrous theophylline content released in thirty minutes. The tablets formed at lower compression forces, might have fairly porous structure, which enables the easy and rapid penetration of dissolution solution into the tablet. Thus, the dispersed drug substance dissolved and were released faster than the dispersed drug content of very dense matrix tablet. As the compression force of tablets was adjusted to 15 kN or 25 kN, the rate of drug release was decreased remarkably in the acidic (pH 1) medium. The last sample was taken after eight hours and until that time approximately 83% of anhydrous theophylline released from the tablets compressed at force of 15 kN. The corresponding value of tablets prepared using compression force of 25 kN was 78%. In basic solution the rate of release of active substance was rapid in spite of higher compression force.

It was possible to control drug release from starch acetate succinate polymer tablet with the magnitude of compression force in tabletting.

EXPERIMENT 6

The effect of drug concentration on the rate of drug release

The rate of drug release of starch acetate matrix tablets containing active substance, i.e. anhydrous theophylline, either 5% (w/w) or 25% (w/w) was examined using the previously described method (Experiment 2.). The experiments were performed both in acidic, is. pH 1, and in basic, pH 8, medium. The degrees of substitution of polymer were 1.34 for acetyl groups and 0.25 for succinyl groups. The compression force used to form matrix tablets was adjusted approximately to 15 kN.

In the basic medium, i.e. phosphate buffer of pH 8, the rate of drug release was fast for both formulations (FIG. 4). About twenty minutes were required for the complete drug release. As the experiment was performed in acidic solution, tablets containing 5% (w/w) of active substance the rate of drug release was somewhat faster compared to the tablets with greater drug amount.

The drug delivery from starch acetate succinate matrices was pH dependent despite the amount of active substance.

EXPERIMENT 7

Drug release from tablets containing equal amounts of separate starch acetate and starch succinate polymers A physical mixture containing 50% (w/w) of starch acetate (DS 2.76) and 50% (w/w) of starch succinate (DS 1.7) was prepared. The polymer tablet matrices compressed at 15 kN force were composed of 74.5% (w/w) polymer mixture, 25% (w/w) anhydrous theophylline and 0.5% (w/w) magnesium stearate. The dissolution testings were accomplished using acidic (pH 1) and basic (pH 8) phosphate buffer solutions.

The release profiles of active substance, over time, from matrices containing starch acetate succinate polymer either in the form of chemical compound or physical mixture are shown in FIG. 5. The degrees of substitution of starch acetate succinate, having the acetyl and the succinyl residues attached to the same starch molecule backbone, were 2.29 and 0.37 for the acetyl and the succinyl groups, respectively. Regardless of the form of polymer content in tablet, anhydrous theophylline release rate was more rapid in basic than in acidic environment (FIG. 5). The amount of succinyl residues was markedly greater in the tablets of physical mixture, which might be the reason for the faster release rate.

Starch acetate succinate content in tablet enabled pH dependent release of active substance. By mixing separate starch acetate and separate starch succinate and using the prepared physical mixture to form matrix tablets, it was also possible to attain the same type of pH dependent controlled drug release.

EXPERIMENT 8

The effect of degrees of substitution of starch acetate succinate polymer on breaking strength of tablets A series of starch acetate succinate, with different degrees of substitution (Table 19.), were compressed at 15 kN force. Besides polymer, tablets were composed of anhydrous theophylline (25% w/w) and magnesium stearate (0.5% w/w). To measure the breaking strength of tablets, a CT-5-tester (Engineering Systems, Nottingham, England) was used.

The acetyl residues appear to be responsible for the mechanical strength of starch acetate succinate tablets (FIG. 6). As the degree of substitution of acetyl groups was above one, the breaking strength was relatively high, indicating good mechanical strength, which was the most important property of pharmaceutical tablets. The compactibility of starch acetate succinate powder seemed to decline with increasing succinyl contents (FIG. 6). The measuring of breaking strength of tablets, compressed from starch acetate succinate No. 4, was not possible because tablets were too weak to handle.

TABLE 19

The degrees of substitution (DS) of different starch acetate succinate.

| Starch acetate succinate | Acetate DS | Succinate DS |
| --- | --- | --- |
| No. 1 | 2.38 | 0.03 |
| No. 2 | 1.34 | 0.25 |
| No. 3 | 1.09 | 0.57 |
| No. 4 | 0.39 | 1.12 |

Acetyl and succinyl groups, attached to the starch molecule, and amount of those groups, i.e. degree of substitution, have influence on the compactibility of starch acetate succinate powder and thus, on the mechanical strength of starch acetate succinate tablets.

EXPERIMENT 9

The effect of compression force on breaking strength of tablets

Three different compression forces were used to prepare tablets of starch acetate succinate, having the degrees of substitution 1.34 for acetyl groups and 0.25 for succinyl groups. The average breaking strength of five tablets compressed at the lowest force, i.e. 5 kN, was about 83N (FIG. 7), indicating reasonable compactibility of polymer. This means that the starch acetate succinate has the ability of powder to form dense, though tablets. The breaking strength of starch acetate succinate tablets increases with rising compression force. The breaking strength values for tablets compressed at 15 kN and 25 kN are about 135N and 153N, respectively.

EXPERIMENT 10

The effect of pH of disintegration medium and compression force on the disintegration time of starch acetate tablets The disintegration time of tablets, containing 74.5% (w/w) starch acetate succinate (degrees of substitution were 1.34 and 0.25 for acetyl groups and succinyl groups, respectively) was determined using the method and apparatus described in the European Pharmacopoeia (Ph. Eur., V. 5.1.1.). Tablets were compressed at three different compression force, i.e. 5 kN, 15 kN and 25 kN. 0.1N hydrochloric acid was used as disintegration medium originally. After operating the apparatus for two hours the acid was replaced by phosphate buffer solution and a disc was added to each tube. pH values were 1.0 and 6.8 for hydrochloric acid and phosphate buffer, respectively.

Starch acetate succinate tablets, prepared at the lowest compression force, i.e. 5 kN, disintegrated already in the acidic medium. The average disintegration time of three tablets was 552 seconds. As the compression forces of 15 kN and 25 kN were used, tablets did not disintegrate completely in acidic solution, even though disruption of tablets in some extent occurred. In FIG. 7 disintegration time in phosphate buffer (pH 6.8) and breaking strength of tablets versus compression force are shown. In spite of the magnitude of compression force, disintegration of tablets was relatively rapid at pH 6.8, which is close to pH of neutral environment (FIG. 7). However, the average disintegration time, i.e. 361 sec., for three tablets prepared with the higher force (25 kN) was obviously longer than the corresponding value, i.e. 112 sec., of tablets compressed at 15 kN force.

Both compression force and pH of disintegration medium seemed to have influence on the disintegration of starch acetate succinate tablets.

EXPERIMENT 11

Microstructure of tablets of starch acetate succinate

The upper surfaces of tablets containing starch acetate succinate with different degrees of substitution, theophylline and magnesium stearate were photographed using an electron scanning microscope (Jeol JSM 35, Tokyo, Japan).

The microstructure of tablets changed clearly with varying degrees of substitution of starch acetate succinate (FIG. 8a–d). Dense, more matrix like structure could be obtained by using polymer with higher acetyl content, i.e. a degree of substitution above two. As the succinyl residue of starch acetate succinate increased and the amount of acetyl groups was low (FIGS. 8a–d), tablets seemed to have more porous structure and thus, poor mechanical strength (Experiment 9). Besides the degrees of substitution of starch acetate succinate, the compression force also had an effect on the microstructure of tablets (FIGS. 9a–c). Three different compression forces, i.e. 5 kN, 15 kN and 25 kN, were used to prepare starch acetate succinate tablets. These tablets contained polymer, which degrees of substitution were 1.34 and 0.25 for the acetyl and the succinyl groups, respectively. As well as polymer content, there were also anhydrous theophylline and magnesium stearate contents in each tablet.

In FIGS. 9a–c, upper surfaces of starch acetate succinate tablets compressed at varying compression forces are shown. As the compression force increased, the structure of tablets became more matrix-like enabling the delayed release of active substance at convenient conditions.

We claim:

1. A composition for pH dependent controlled release of an active ingredient comprising of a compactible mixture of an active ingredient and starch molecules substituted with acetate and dicarboxylate residues.

2. The composition of claim 1, wherein the dicarboxylate residue is selected from a group consisting of oxalate, malonate, succinate, glutarate, adipate, pimelate, suberate, azealate, sebacate, maleate, fumarate, malate, tartrate, citrate and mixtures thereof.

3. The composition of claim 1, wherein the dicarboxylate residue is succinate.

4. The composition of claim 1, wherein the starch molecules have an average substitution degree of at least 1 for the acetate residue.

5. The composition of claim 1, wherein the starch molecules have an average substitution degree of at least 1.5 for the acetate residue.

6. The composition of claim 1, wherein the starch molecules have an average substitution degree of at least 2 for the acetate residue.

7. The composition of claim 1, wherein the starch molecules have an average substitution degree between about 1.00–2.95 for the acetate residue.

8. The composition of claim 1, wherein the starch molecules have an average substitution degree of 0.05–1.5 for the dicarboxylate residue.

9. The composition of claim 1, wherein the starch molecules have an average substitution degree of 0.1–1.2 for the dicarboxylate residue.

10. The composition of claim 1, wherein the starch molecules have an average substitution degree of 0.2–1.0 for the dicarboxylate residue.

11. The composition of claim 1, wherein the starch molecules have the acetate and dicarboxylate residues attached to the same starch molecule backbone.

12. The composition of claim 1, wherein the starch molecules have the acetate and dicarboxylate residues on separate starch molecule backbones.

13. The composition of claim 1, wherein the release of the active ingredient is retarded in an acidic solution.

14. The composition of claim 1, wherein the release of the active ingredient is enhanced in an essentially neutral pH or basic pH.

15. A method for preparing the composition of claim 1 comprising the steps of:
a) preparing starch acetate molecules;
b) substituting part of the acetate residues in the starch acetate molecules obtained in step a) with dicarboxylate residues using transesterification methods to obtain starch acetate dicarboxylate molecules;
c) mixing the starch acetate dicarboxylate molecules obtained in step b) with an active ingredient;
d) compressing said mixture obtained in step c) to provide a compact for controlled release of the active ingredient.

16. The method of claim 15, wherein the dicarboxylate residues are selected from a group consisting of oxalate, malonate, succinate, glutarate, adipate, pimelate, suberate, azealate, sebacate, maleate, fumarate mealate, tartrate, citrate or mixture thereof.

17. The method of claim 15, wherein the dicarboxylate residue is succinate.

18. A method for preparing the composition of claim 1 comprising the steps of:
a) preparing starch dicarboxylate molecules;
b) substituting part of the dicarboxylate residues of the starch dicarboxylate molecules obtained in step a) with acetate residues using transesterification methods to obtain starch acetate dicarboxylate molecules;
c) mixing the starch acetate dicarboxylate obtained in step b) with an active ingredient;
d) compressing said mixture obtained in step c) to provide a compact for controlled release of the active ingredient.

19. The method of claim 18 wherein the dicarboxylate residues are selected from a group consisting of oxalate, malonate, succinate, glutarate, adipate, pimelate, suberate, azealate, sebacate, maleate, fumarate, malate, tartrate, citrate and mixture thereof.

20. The method of claim 18, wherein the dicarboxylate residue is succinate.

21. A method for preparing the composition of claim 1 comprising the steps of:
a) by allowing starch to react with a mixture of reactive acetyl and dicarboxyl groups;
b) mixing the active ingredient and the product obtained in step a)
c) compressing the product obtained in step b) to obtain a compact for control release of the active ingredient.

22. The method of claim 21, wherein the dicarboxylate residues are selected from a group consisting of oxalate, malonate, succinate, glutarete, adipate, pimelate, suberate, azealate, sebacate, maleate, fumarate, malate, tartrate, citrate and mixture thereof.

23. The method of claim 21, wherein the dicarboxylate residue is succinate.

24. A method for preparing the composition of claim 1 comprising the steps of:
a) preparing a starch acetate;
b) preparing a starch dicarboxylate;
c) mixing the starch acetate obtained in step a), the starch dicarboxylate obtained in step b) with an active ingredient;
d) compressing the mixture obtained in step c) to obtain a compact for control release of the active ingredient.

25. The method of claim 24, wherein the dicarboxylate residues are selected from a group consisting of oxalate, malonate, succinate, glutarate, adipate, pimelate, suberate, azealate, sebacate, maleate, fumarate, malate, tartrate, citrate and mixture thereof.

26. The method of claim 24, wherein the dicarboxylate residue is succinate.

27. The composition of claim 1, wherein part of the starch molecules substituted with acetate and dicarboxylate residues can be replaced by native starch or modified starch.

28. The composition of claim 12, wherein part of the starch molecules substituted with acetate residues can be replaced by native starch or modified starch.

29. The use of the composition of claim 1 for the preparation of tablets for enteric use.

30. A composition for pH dependent controlled release of an active ingredient, comprising a compactible mixture of an active ingredient and starch molecules substituted with acetate and dicarboxylate residues, wherein the minimum DS of acetate is a DS which provides the tablet with sufficient controlled release properties and mechanical strength, and the minimum DS of dicarboxylate is a DS sufficient to give a detectable pH dependent release.

* * * * *

UNITED STATES PATENT AND TRADEMARK OFFICE
CERTIFICATE OF CORRECTION

PATENT NO. : 5,656,292
DATED : Aug. 12, 1997
INVENTOR(S) : Arto Olavi Urtti et al.

It is certified that error appears in the above-identified patent and that said Letters Patent is hereby corrected as shown below:

Cover page, column 1, line [73], delete "Alko Group Ltd., Helsinki, Finland" and insert therefor --Oy Polymer Corex Kuopio Ltd., Kuopio, Finland--.

Signed and Sealed this

Seventeenth Day of March, 1998

Attest:

BRUCE LEHMAN

*Attesting Officer*  *Commissioner of Patents and Trademarks*